(12) United States Patent
Berti

(10) Patent No.: US 7,483,512 B2
(45) Date of Patent: Jan. 27, 2009

(54) VARIABLE CENTRE DIFFRACTOMETER

(76) Inventor: Giovanni Berti, Via Piero di Puccio, 3-56126 Pisa (IT)

( * ) Notice: Subject to any disclaimer, the term of this patent is extended or adjusted under 35 U.S.C. 154(b) by 0 days.

(21) Appl. No.: 11/815,249

(22) PCT Filed: Jan. 31, 2006

(86) PCT No.: PCT/EP2006/050560

§ 371 (c)(1),
(2), (4) Date: Nov. 1, 2007

(87) PCT Pub. No.: WO2006/082187

PCT Pub. Date: Aug. 10, 2006

(65) Prior Publication Data

US 2008/0130832 A1 Jun. 5, 2008

(30) Foreign Application Priority Data

Feb. 2, 2005 (IT) ............................. FI2005A0016

(51) Int. Cl.
*G01N 23/20* (2006.01)
*G01N 23/207* (2006.01)
*G21K 1/06* (2006.01)

(52) U.S. Cl. ............................. 378/70; 378/73; 378/84

(58) Field of Classification Search .............. 378/70–85
See application file for complete search history.

(56) References Cited

U.S. PATENT DOCUMENTS 6,064,717 A 5/2000 Ortega et al.
6,301,330 B1 * 10/2001 Kurtz et al. .................... 378/71
6,792,075 B2 * 9/2004 Kozaczek et al. ............. 378/71
2004/0228440 A1 * 11/2004 Vigliante ..................... 378/71

FOREIGN PATENT DOCUMENTS

WO WO0140876 6/2001
WO WO03060498 7/2003

OTHER PUBLICATIONS

Dhez P et al: "Instrumental Aspects of X-Ray Microbeams in the Range Above 1 keV" Review of Scientific Instruments, AIP, Melville, NY, US, vol. 70, No. 4, Apr. 1999, pp. 1907-1920, XP000875395 ISSN: 0034-6748 figures 6,7.

* cited by examiner

Primary Examiner—Irakli Kiknadze

(57) ABSTRACT

A diffractometer, having variable center and suitable for performing analysis on hidden or hardly accessible bodies or specimens is described. Said variable center diffractometer is equipped with an analytical unit that comprises: a circle arc structure, called Euler cradle; a radiation beam source and a detector of the said radiation beam; devices for the pointing of the analytical unit; devices for the movements of said analytical unit in the space; devices for rotation of said source and detector along the Euler cradle; characterized by the fact that it comprises also: devices able to rotate said source and detector with respect to an orthogonal axis to the plane containing the Euler cradle; collimators or deflectors firmly placed on the said radiation source and detector.

12 Claims, 1 Drawing Sheet

VARIABLE CENTRE DIFFRACTOMETER

The following foreign priority application(s) are hereby incorporated by reference in their entirety:
Italian Application No. FI2005A000016, filed Feb. 2, 2005; and
PCT Application No. PCT/EP06/050560, filed Jan. 31, 2006.

FIELD OF THE INVENTION

The current invention concerns a diffractometer, in particular an X ray diffractometer in which the X ray source and the detector have moving devices and collimation devices.

PRIOR ART

In the patent application MI2002A000097 a diffractometer is described in which the radiation source and the detector are placed on the analytical unit and pointing toward the centre of the same analytical unit; said centre is placed at a fixed distance from the end-line of the analytical unit.

Although the efficiency of the instrument for analysis on easily accessible components is demonstrated, this instrument is not suitable for performing analysis on hidden or hardly accessible bodies or specimens.

In some case, for example, analysis must be performed on gears, or on components of other nature, installed at the inside of holders or in components with a particular geometry, which are not easily reachable using traditional investigations means, as figures or shape in relief or in caves.

In these cases, although the number of freedom degrees of source and detector is high, it is not possible to match the goniometer centre with the object to be analysed and consequently it's impossible to obtain measures with such an instrument.

SUMMARY OF THE INVENTION

A diffractometer comprising a movement systems of source and detector and collimators or deflectors which are firmly attached to the source and detector.

DETAILED DESCRIPTION OF THE INVENTION

Figure 1:
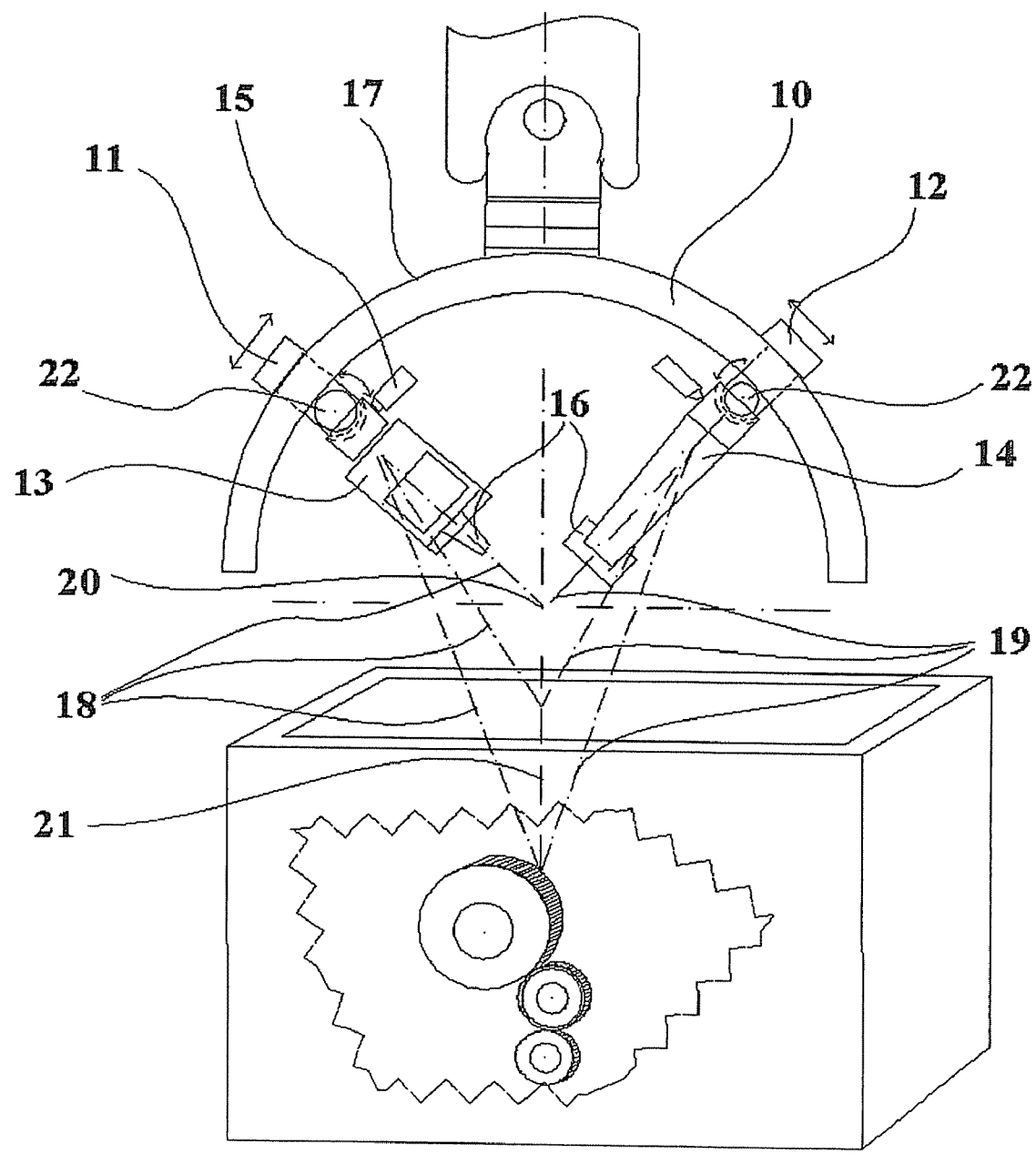
FIG. 1 represents the scheme of the bottom part of the analytical unit of the diffractometer according to the invention; it illustrates also the position of the incident and detection axes obtained when rotating the source and detector; the figure shows also the advantageous use of diffractometer according to the invention.

This invention overcomes the above mentioned problems thanks to the presence of devices able to move either the source or the detector and collimators (or deflectors) solidly applied to the radiation source and the detector.

As said above, according to the present invention, the diffractometer, is essentially composed by a diffractometer, as described in the above mentioned application MI2002A00097, equipped with an analytical unit that includes:
a circle arc structure, called Euler cradle;
a radiation beam source and a detector of the said radiation beam;
pointing devices of the analytical unit;
moving devices of said analytical unit in the space;
devices to rotate said source and detector along the Euler cradle;
but it also comprises
devices able to rotate said source and detector with respect to an axis which is orthogonal to the plane containing the cradle and collimators or deflectors solidly applied to these source and detector.

As seen in FIG. 1, the analytical unit of the diffractometer, according to the present invention, comprises an element 10, called Euler cradle, and two arms 11 and 12 that engage with the mentioned Euler cradle 10 and can move along its border.

To these arms 11 and 12 are applied devices 15 that can rotate each of these wrists 22 around an axis perpendicular to the plane containing the Euler cradle.

On the source 13, and eventually even at the detector 14, are solidly applied collimators and deflectors 16.

Preferably the Euler cradle is a circle arc with toothed borders 17 that can engage with the arms 11 and 12.

The devices 15, for example, can be step motors; otherwise, the source 13 and the detector 14 can be placed on a small rotating platform firmly hinged on the arms 11 and 12.

As already described in the application above mentioned, the pointing devices are placed on the Euler cradle and useful for pointing the instrument with respect to the system (or component) under analysis; they are for example cameras, laser, and equivalents.

According to the invention, collimators are preferable polycapillaries (as lens, half lens, or other) while deflectors are, for example, graded multilayer mirrors.

According to the invention, the use of polycapillaries, preferable with lens (in order to focalise the beam) or half-lens (when a beam parallel to a propagation direction is required), are useful to reduce the beam divergence and increase the radiation density on the specimen under analysis. Multilayer and graded mirrors can be properly used for beam collimation and to improve the irradiation on the analyzed specimen.

The advantage obtained from the configuration named "variable centre" are represented by the flexibility of uses and applications of the instrument.

In fact in any of the known diffractometers, for any position of source and detector on the Euler cradle, the collimation axis 18 of the source 13 and the receiving axis 19 of the detector 14 are direct towards a point 20, that is the diffractometer centre (that, for example, can match with the curvature centre of the Euler cradle) where the specimen under investigation shall be.

According to the present invention, using the present diffractometer, it is possible to point the beam and the direction of the detector towards a target which is not necessarily placed in the diffractometer centre. According to a preferred embodiment of the invention, the beam can be made parallel to a propagation direction thorough the use of polycapillaries (half-lens) or graded multilayer mirrors.

The source 13 and the detector 14 can rotate around their respective axis; these axes are perpendicular to the plane of the Euler cradle; when the source (the collimation axis 18) and the detector (receiving axis 19) are positioned at the angle (?) with respect to the observation axis (21), their rotation (a) around to the axes which are orthogonal to the collimation and receiving ones, allow to reach a depth (p) given by the formula:

$$(p) = [a \operatorname{sen} ?(\operatorname{ctg}(?-a) - \operatorname{ctg} ?].$$

where a is the diffractometer radius, tg and ctg are respectively the trigonometric tangent and cotangent, and (a) and (?) are defined as above.

So in this case, said point 20 will move along the observation axis 21, generated by the intersection of the axis 17 and 18 and normal to the intersection between the equatorial plane (coinciding with the drawing plane) and the axial plane which is perpendicular to it.

Preferable, said observation axis 21 passes through the Euler cradle centre, as represented in FIG. 1.

So in this case, unlike the already known instrument, the centre is not fixed but actually variable.

By this device it is possible to analyse bodies or specimens that could not be irradiated (and so analysed) when using the instrument at the previous state of art because it would not be possible to put the above mentioned bodies or specimen in the centre of the usual analytical unit.

The invention concerns also a diffractometry method, preferable X rays diffraction, in which the diffractometer as above mentioned is used.

FIG. 1 represents schematically the usefulness and versatility of the diffractometer according to the invention.

In fact, let us consider the case when it is requested to perform analysis on hardly reachable devices (see figure) which therefore does not allow to be positioned on the fixed focus equipment (as it is the case of the traditional diffractometer).

By the present diffractometer, it is possible to move the diffractometer centre and reach each point of the device under investigation by moving the source and the detector along the Euler cradle and then by rotating them mutually opposite around the wrist 22.

In the due course of the measure the movement of the source 13 and the detector 14, will develop along the Euler cradle in the same way as described for the above diffractometer while for each angle (?), the pointing of the source 13 and the detector 14 can be rotate for one quantity $$?=?-\text{arctg}\,[p/(a\,\text{sen}\,?\,\text{ctg}?)]$$

where a, p and ? are as above mentioned and actg is the trigonometric arc tangent.

I claim:

1. A variable centre diffractometer equipped with an analytical unit, comprising:
   a circle arc structure, called a Euler cradle;
   a radiation beam source and a detector of the said radiation beam;
   devices for the pointing of the analytical unit;
   devices for the movements of said analytical unit in a space;
   devices for rotation of said source and detector along the Euler cradle, further comprising
      devices able to rotate said source and detector with respect to an orthogonal axis to a plane containing the Euler cradle; and
      collimators placed on said radiation source and detector.

2. The diffractometer according to claim 1 in which said source and detector are applied through wrists to two arms that work with the Euler cradle and are able to slide along a border of said cradle.

3. The diffractometer according to claim 2 in which the arms are firmly applied devices able to rotate each of said wrists around an axis perpendicular to the plane containing the Euler cradle.

4. The diffractometer according to claim 1 in which the devices are able to rotate said wrists include step motors.

5. The diffractometer according to claim 1 in which said collimators include polycapillaries.

6. The diffractometer according to claim 5 in which the polycapillaries have a lens shape.

7. The diffractometer according to claim 5 in which the polycapillaries have a half lens shape.

8. A method of diffractometric analysis, comprising
   providing an analytical unit including a circle arc structure, called a Euler cradle;
   providing a radiation beam source and a detector of the said radiation beam;
   pointing the analytical unit under the control of a plurality of pointing devices;
   controlling movements of said analytical unit in a space;
   rotating said source and detector along the Euler cradle, including
      rotating the source and detector with respect to an axis orthogonal to a plane containing the Euler cradle; and
      placing collimators or deflectors on the radiation source and detector.

9. The method according to claim 8 in which the diffractometer is an X-ray diffractometer.

10. The method according to claim 8 in which source and detector rotate along the Euler cradle.

11. A variable centre diffractometer equipped with an analytical unit, comprising:
   a circle arc structure, called a Euler cradle;
   a radiation beam source and a detector of the said radiation beam;
   devices for the pointing of the analytical unit;
   devices for the movements of said analytical unit in the space;
   devices for rotation of said source and detector along the Euler cradle, further comprising
      devices able to rotate said source and detector with respect to an orthogonal axis to a plane containing the Euler cradle; and
      deflectors placed on the said radiation source and detector.

12. The diffractometer according to claim 11 in which said deflectors include graded multilayer mirrors.

* * * * *